United States Patent
Bleam

(10) Patent No.: US 6,251,094 B1
(45) Date of Patent: Jun. 26, 2001

(54) CATHETER HAVING OPTIMIZED BALLOON TAPER ANGLE

(75) Inventor: Jefferey Bleam, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/088,960

(22) Filed: Jun. 2, 1998

Related U.S. Application Data

(62) Division of application No. 08/698,094, filed on Aug. 15, 1996.

(51) Int. Cl.[7] .................................................. A61M 29/00
(52) U.S. Cl. ......................................................... 604/96.01
(58) Field of Search .............................. 604/96.01, 103, 604/101.01, 101.02, 101.03, 101.04, 101.05, 915, 916, 917, 918; 606/192, 194

(56) References Cited

U.S. PATENT DOCUMENTS

| | | |
|---|---|---|
| 5,320,634 | 6/1994 | Vigil et al. . |
| 5,334,146 | 8/1994 | Ozasa . |
| 5,370,618 | 12/1994 | Leonhardt . |
| 5,378,237 | 1/1995 | Boussignac et al. . |
| 5,456,666 | 10/1995 | Campbell et al. . |
| 5,571,087 | 11/1996 | Ressemann et al. . |
| 5,653,230 | 8/1997 | Ciaglia et al. . |

OTHER PUBLICATIONS

U.S. application No. 09/470,075, Lee, filed Feb. 16, 2000.

*Primary Examiner*—Manuel Mendez
(74) *Attorney, Agent, or Firm*—Blakely, Sokoloff, Taylor & Zafman LLP

(57) ABSTRACT

A dilation catheter and expandable balloon. The catheter includes a catheter tube, a proximal end, a distal end and an axis which extends between the proximal and distal ends. A balloon has two ends, at least one end mounts on the distal end of the catheter. The balloon inflates and deflates between a collapsed configuration and an expanded configuration. The balloon has a tapered portion and a working length. The tapered portion extends from the catheter tube at an angle α within the range of 7° to 20° and attaches the working length of the balloon to the catheter tube. Accordingly, the angle α between the tapered portion and the catheter tube is optimized to enable the balloon to slide when the balloon is in the collapsed configuration.

5 Claims, 4 Drawing Sheets

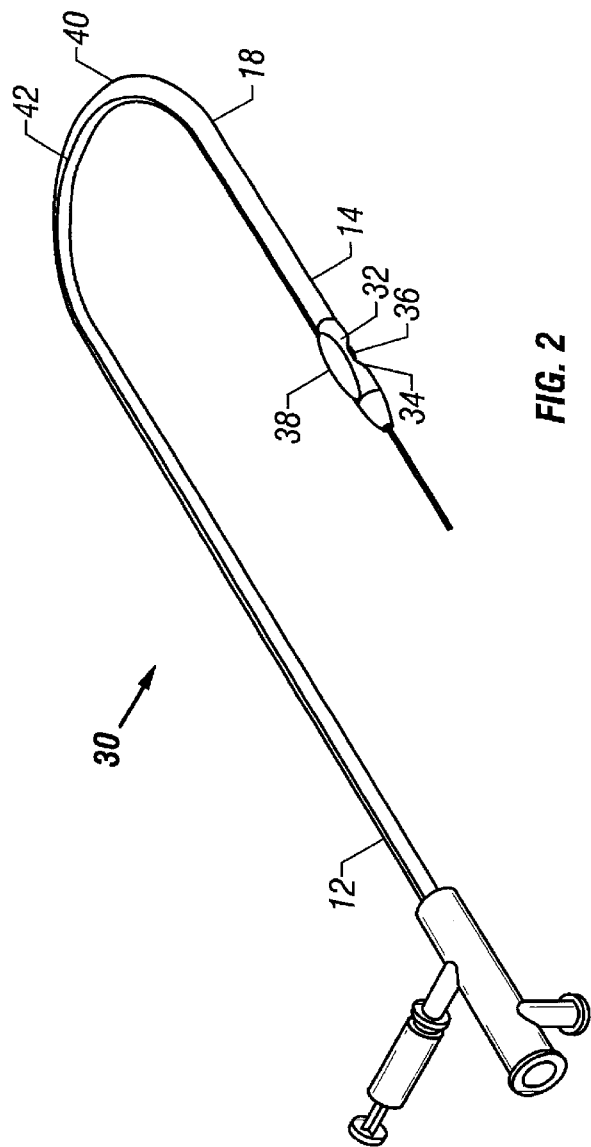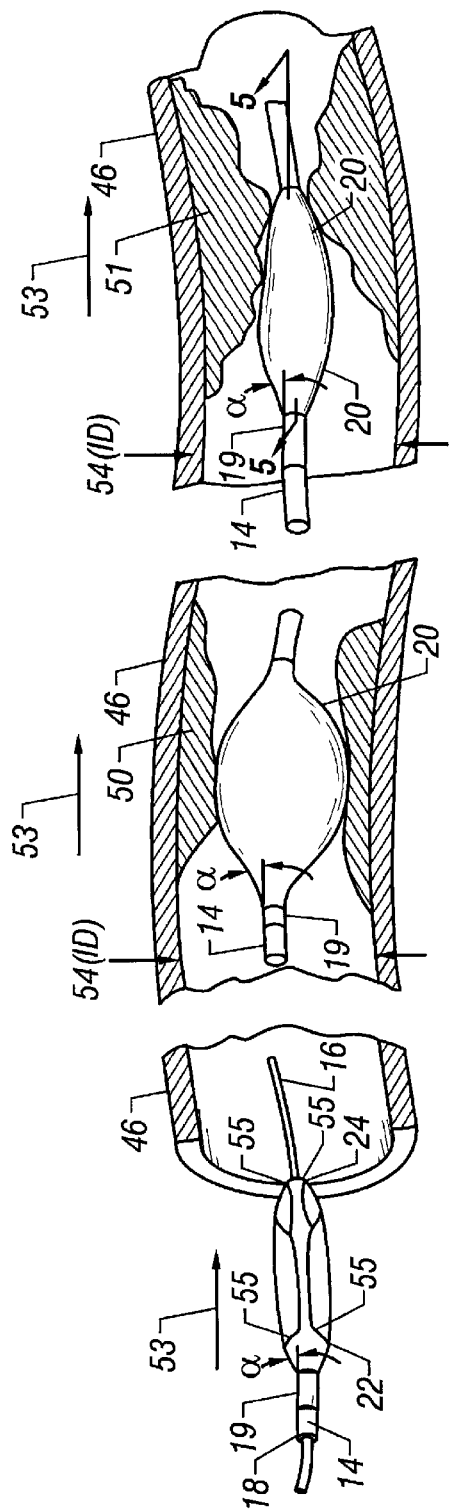

CATHETER HAVING OPTIMIZED BALLOON TAPER ANGLE

This application is a divisional of copending U.S. Non-provisional Patent Application No. 08/698,094, filing date Aug. 15, 1996

CROSS-REFERENCE TO RELATED PATENTS

The present invention relates in subject matter to U.S. Pat. No. 4,582,181 (Samson); U.S. Pat. No. 5,350,395 (Yock); U.S. Pat. No. 5,242,399 (Lau et al.); U.S. Pat. No. 5,348,545 (Shani et al); U.S. Pat. No. 5,334,154 (Samson et al.) and U.S. Pat. No. 5,480,383 (Bagaoisan et al), The disclosures of these related patents are incorporated herein by reference.

BACKGROUND OF THE INVENTION

1. Field of the Invention

This invention relates generally to dilation catheters. More particularly, this invention relates to intravascular catheter balloons.

2. Previous Art

Various dilation catheters rely upon an inflatable balloon for applying pressure against the interior of a biological conduit such as a blood vessel. These inflatable balloons come in various shapes and sizes to perform any of a number of functions. For example, dilation catheters are used in percutaneous transluminal coronary angioplasty (PTCA); vascular prosthesis implantation; atherectomy and various other medical procedures.

In classical PTCA, a hollow guiding catheter, a guidewire and a dilation catheter are inserted into the vasculature of a patient. The guiding catheter has a pre-shaped distal tip which is percutaneously introduced into the vasculature and advanced. An operator, such as a surgeon, twists and moves the proximal end of the guiding catheter to advance the distal tip through the aorta. The distal tip reaches the ostium of a diseased coronary artery. An example of a guiding catheter and the operation thereof is disclosed in U.S. Pat. No. 5,348,545 (Shani et al), the disclosure of which is incorporated herein by reference.

While the distal end of the guiding catheter is seated in the ostium, the guidewire advances out the distal tip of the guiding catheter into the diseased coronary artery. The operator twists the proximal end of the guidewire to guide the curved distal end of the guidewire. The operator advances the guidewire within the coronary anatomy until the shaped distal end of the guidewire enters the diseased coronary artery. The diseased artery may include a stenosed region having a lesion, for example. This advancement of the guidewire continues until the guidewire crosses a lesion, prosthetic implant or other region to be dilated.

The dilation catheter slides over the guidewire and through the guiding catheter. The dilation catheter then advances out of the distal tip of the guiding catheter, over the previously advanced guidewire until the balloon on the distal end of the dilation catheter is properly positioned adjacent to the lesion.

Fluid inflates the balloon to a predetermined size. The fluid often pressurizes the balloon at pressures which may reach 20 atm but which are often within the range of 4–12 atm. Conventional balloon designs have two ends attached to the catheter, a working length and a tapered portion. The tapered portion extends between the balloon end and the working length. Accordingly, the tapered portion defines a transition between the shaft and the balloon end and the working length.

The angle at which tapered portion extends from the catheter is typically greater than 200. The length of the taper (taper length) is typically less than 3 mm.

A variety of dilation catheters exist which may have different purposes including prosthetic implantation, angioplasty, atherectomy, diagnostic procedures and even various re-vascularization techniques which are being developed. Rapid exchange and over the wire types of dilation catheters are two common types of dilation catheters. Examples of various dilation catheters having a balloon are disclosed in U.S. Pat. No. 4,582,181 (Samson); U.S. Pat. No. 5,350,395 (Yock); U.S. Pat. No. 5,242,399 (Lau et al.); U.S. Pat. No. 5,334,154 (Samson et al.) and U.S. Pat. No. 5,480,383 (Bagaoisan et al). The disclosures of these patents are incorporated herein by reference.

Multiple lesions may exist in a diseased coronary artery. It is desirable to move the deflated balloon across any number of these lesions to optimally position the balloon within the artery for inflation against a selected lesion. With known balloon designs the deflated balloon may experience considerable frictional force between the balloon and the lesion when the balloon crosses the lesion. These are known as cross forces. During withdrawal of the balloon, the balloon may similarly experiences such frictional forces across the lesion. These forces are known as recross forces. Cross and recross forces are sought to be minimized.

Cross and recross forces may inhibit smooth movement of the deflated balloon within the vasculature of a patient, cause thrombus buildup, and may be uncomfortable to the patient. Additionally, if the patent has a stent located near the crossed or recrossed lesion, the cross and recross forces may dislodge the stent. Given that stent implantation is becoming more common, ways to avoid stent dislodgment are increasingly important considerations for balloon designers.

What is desired is an improved balloon design which more easily crosses lesions while the balloon is deflated. What is also desired is an improved balloon which reduces cross and recross forces.

SUMMARY OF THE INVENTION

It is an object of this invention to provide a balloon which is optimized to slide within a biological conduit such as a blood vessel.

It is a further object of this invention to provide a balloon having a taper angle which minimizes the cross and recross forces between the balloon and a blood vessel.

In accordance with the above objects and those that will be mentioned and will become apparent below, an apparatus for insertion into a biological conduit, comprises:

- a catheter tube having a proximal end, a distal end and an axis which extends between the proximal and distal ends; and
- a balloon, the balloon being mounted on the distal end of the catheter, the balloon expanding from a collapsed configuration to an expanded configuration,
- the balloon has a tapered portion and a working length, the tapered portion connecting the working length with the catheter tube, the tapered portion extending from the catheter tube at an angle which remains within the range of 7° and 20 whether the balloon is in an expanded, collapsed or deformed configuration,
- whereby, the angle is optimized to enable the balloon to slide within the biological conduit.

In a preferred embodiment, the tapered portion extends from the catheter tube at an angle within the range of 9° and 12°. Preferably, the tapered portion extends from the catheter tube at an angle within the range of 10° and 11°.

In another preferred embodiment, the balloon has a taper length within the range of 3.0 mm and 9.0 mm. Preferably, the balloon has a taper length within the range of 5 mm to 7 mm.

In another preferred embodiment, the balloon has a double wall thickness within the range of 1.00–2.00 mm. It can be appreciated that the double wall thickness is dependent on the material from which the balloon is fabricated. This double wall thickness range is associated with balloons made from nylon, PET, and PE, for example. Such materials are contemplated in various embodiments of the present invention.

In another preferred embodiment, the tubular member includes an inflation lumen extending between the proximal end of the tubular member and the balloon. The inflation lumen delivers fluid to the balloon to inflate the balloon into the expanded configuration and withdraws fluid from the balloon to deflate the balloon into the collapsed configuration.

In another preferred embodiment, the tapered portion extends from the catheter tube at an angle within the range of 9° to 12°. In a variation of this embodiment, the tapered portion extends from the catheter tube at an angle within the range of 10° to 11°.

In another preferred embodiment, the balloon has a taper length within the range of 3.0 to 9.0 mm. In a variation of this embodiment, the balloon has a taper length within the range of 5.0 to 7.0 mm.

An advantage of this invention is to provide a balloon which is optimized to slide within a biological conduit such as a blood vessel. A further advantage of this invention is to provide a balloon having a taper angle which minimizes cross-recross forces experienced by the balloon, whether the balloon is inflated, deflated or deformed.

BRIEF DESCRIPTION OF THE DRAWING

For a further understanding of the objects and advantages of the present invention, reference should be had to the following detailed description, taken in conjunction with the accompanying drawing, in which like parts are given like reference numerals and wherein:

FIG. 2 is a perspective view of an atherectomy catheter in accordance with the present invention.

FIGS. 3a–3c are cross-sectional views of insertion of the angioplasty catheter of FIG. 1 into a biological conduit.

DETAILED DESCRIPTION OF THE INVENTION

Figure 1:
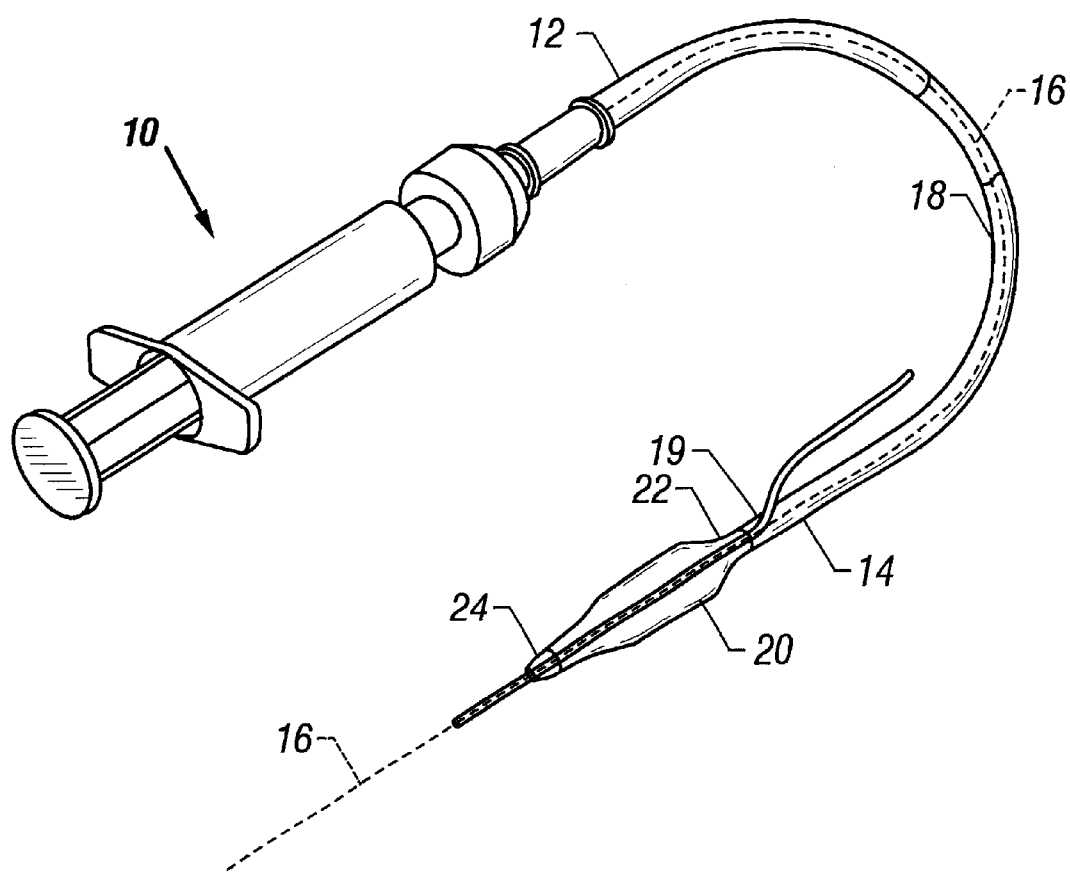
FIG. 1 is a perspective view of an angioplasty catheter having a balloon in accordance with the present invention.

The invention will now be described with respect to FIG. 1, which illustrates a balloon dilation catheter in accordance with the present invention, shown generally by the reference numeral 10. The catheter 10 has a proximal end 12, a distal end 14, an axis 16 and a catheter tube 18. The catheter tube 18 extends between the ends 12 and 14 along the axis 16.

A balloon 20 mounts on the distal end 14 of the catheter 10. The balloon 20 has a proximal end 22 and a distal end 24. The ends 22 and 24 of the balloon 20 parallel the catheter axis 16. The balloon 20 is inflatable to expand from a collapsed configuration to an expanded configuration. The balloon 20 is deflatable after inflation to selectively return to the collapsed configuration.

The balloon 20 is fabricated from a flexible polymer such as nylon, PET, PE, etc. The balloon 20 has ends 22 and 24. In one embodiment, the ends 22 and 24 are formed integrally with the catheter tube 18. In another embodiment, the end 22 includes a balloon shaft 19 which bonds to the catheter tube 18 by adhesive or heat bonding. Examples of catheters having a balloon 20 are disclosed in U.S. Pat. No. 4,582,181 (Samson); U.S. Pat. No. 5,350,395 (Yock); U.S. Pat. No. 5,334,154 (Samson et al.) and U.S. Pat. No. 5,480,383 (Bagaoisan et al). The disclosures of these patents are incorporated herein by reference.

The catheter 10 is adapted for percutaneous transluminal coronary angioplasty procedures (PTCA). Although the catheter 10 is adapted for PTCA, it can be appreciated that a balloon in accordance with the present invention can be used in conjunction with many other procedures including the implantation and repair of intraluminal (e.g. intravascular) prostheses. An example of a dilation catheter for repairing an intravascular prosthesis is disclosed in U.S. Pat. No. 5,242,399 (Lau et al.), the disclosure of which is incorporated herein by reference. The Lau patent discloses a dilation catheter for delivering an intravascular prosthesis to an occluded region of the vasculature of a patient.

It can be appreciated that the balloon 20 and catheter 10 of the present invention have multiple applications. Such applications include diagnostic procedures such as cardiological and vascular imaging. Other uses include laser and mechanical ablation of biological tissue, transluminal medication delivery, and various other interventional, diagnostic and corrective procedures.

With particular reference to FIG. 2, there is shown an atherectomy catheter 30 in accordance with the present invention. The catheter 30 includes a catheter tube 18; a work element housing 32 attached to the catheter tube 18; a balloon 38 attached to the housing 32; a window 34 formed in the housing 32; and a work element 36 disposed within the housing 32. The window 34 exposes the work element 36.

The balloon 38 of the catheter 30 performs multiple functions. The balloon 38 holds the work element 36 in a desired position within the cardiovascular system. Additional possible uses of a balloon include holding and repositioning a work element 36 within a biological conduit. It can be appreciated that the work element 36 may include tools in addition to the atherectomy cutter. The work element 36 may have an imaging device, or a drug delivery system, for example.

The balloon 38 mounts on a lateral side of the housing 38, opposing the window. In operation, the balloon 38 is normally collapsed during insertion of the catheter 30 into a biological conduit. However, when the catheter 30 is positioned as desired with the biological conduit, the balloon 38 inflates and expands to hold the distal end of the catheter 30 in a desired position within the biological conduit. The balloon 38 adjusts the position of the housing 32 with respect to the biological conduit.

The catheter tube 18 includes an inflation lumen 42 extending between the proximal end 12 of the catheter 30 and the balloon 38. The inflation lumen 42 delivers fluid to the balloon 38 to inflate the balloon 38 into the expanded configuration. An example of an atherectomy catheter having an inflatable balloon is disclosed in U.S. Pat. No. 5,429,136 to Milo et al., the disclosure of which is incorporated herein by reference.

With particular reference to FIGS. 3a–3c, there is shown the distal end 14 of the angioplasty catheter 10 inserting into a blood vessel 46. The distal end 14 inserts in stages as will be described with respect to FIGS. 3a, 3b, and 3c, respectively.

In FIG. 3a, the balloon 20 is collapsed, having an optimal profile for insertion into the blood vessel 46. When the balloon 20 collapses, the balloon 20 assumes a flattened configuration and curls around the distal end 14. The balloon 20 remains flattened and curled upon entry into the blood vessel 46. During insertion, the balloon 20 will typically remain generally flat and curled, however, after inflation at high pressures, the balloon 20 and may fold or form surface wrinkles.

The collapsed balloon has lateral edges 55 which curl and stay curled as the balloon 20 inserts through the blood vessel 46. With the edges 55 curled, the balloon 20 attains a generally tubular configuration. It can be appreciated that the edges 55 uncurl as the balloon 20 inflates.

While the balloon 20 is collapsed, the lateral edges 55 define the taper angle α which extends from the balloon shaft 19. The edges 55 are defined on the proximal end 22 and the distal end 24 of the balloon 20. The taper angle α minimizes friction between the balloon 20 and the blood vessel 46. The taper angle α eases insertion of the catheter 10 through the blood vessel 46.

In the second stage, shown particularly by FIG. 3b, the balloon 20 inserts into the blood vessel 46 and inflates. Inflation of the balloon 20 expands the inside diameter (ID) 54 of the blood vessel 46 at the situs of the lesion 50. The balloon 20 holds the distal end 24 of the catheter in the blood vessel 46. The balloon 20 also compresses the lesion 50 against the ID 54 of the blood vessel 46. Compression of the lesion optimally restores normal blood flow through the blood vessel 46. It can be appreciated, however, that in other aspects of the invention, the balloon 20 may be adapted for inserting and expanding an intraluminal prosthesis, to hold a medical device within a lumen, or other purposes.

As shown in FIG. 3c, and after compression of the lesion 50, the balloon 20 deflates into the collapsed configuration. The balloon 20 ideally will deflate and the edges of the balloon will curl the balloon 20 into a cylindrical shape as shown in FIG. 3a. Often, however, the balloon 20 will deform as shown. Deformation of the balloon is typically due to high pressures experienced during inflation (e.g. 10–20 atm.). The deformed balloon 20 has a flat portion which is generally flat and the edges may curl less than shown in FIG. 3a.

The taper angle α is optimized to enable the deformed balloon 20 to move through the blood vessel 46 with minimal force. Accordingly, the balloon 20 may further insert through the blood vessel 46 to the next lesion 51. The process of expanding the inside diameter (ID) 54 repeats at the site of the lesion 51.

Reciprocally moving the catheter 10 across lesions causes frictional forces between the lesion 51 and the balloon 20. These frictional forces are termed cross-recross (CRC) forces. The taper angle α is optimized to minimize the cross-recross forces when the balloon 20 is in the collapsed configuration whether the balloon is deformed or not. The taper angle α as measured when the balloon 20 is in the collapsed configuration is the approximately the same angle as measured when the balloon 20 is expanded, collapsed or deformed. Although the taper angle α is optimized to reduce CRC forces when the balloon crosses a lesion, it can be appreciated that the taper angle α also has the effect of reducing friction between healthy portions of a blood vessel and the balloon 20. The taper angle ca is maintained while the balloon 20 expands and collapses.

The terms "collapsed" and "collapsed configuration" indicate that the balloon 20 is not fully expanded. The collapsed balloon 20 holds a volume of fluid which is significantly less than the volume of fluid held by the balloon 20 when expanded. A typical expanded balloon 20 may hold pressure of 10–20 atm, for example. A collapsed balloon may hold pressure of less than 1 atm. It can be appreciated that the pressures at which the balloon inflates and deflates may vary in accordance with the particular catheter and balloon design requirements.

Figure 4:
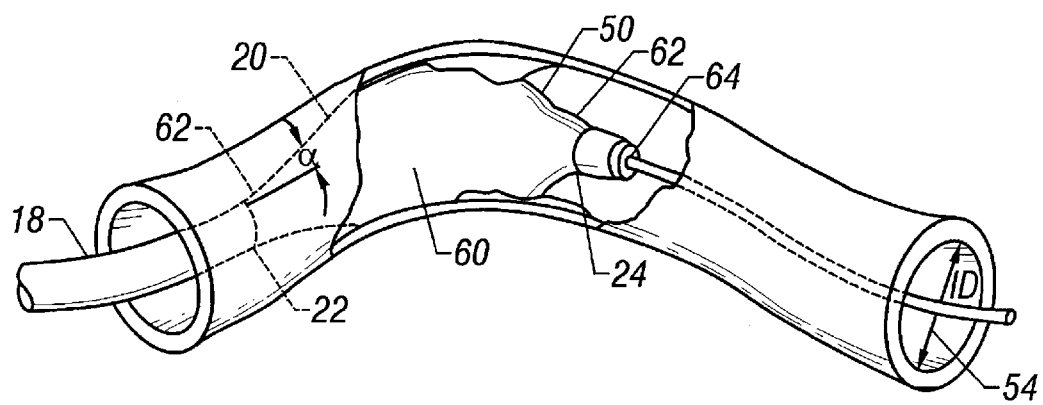
FIG. 4 is an enlarged partially cut away perspective view of the angioplasty catheter of FIG. 1 in a biological conduit with the balloon in the expanded configuration.

With particular reference to FIG. 4, there is shown the balloon 20 of FIG. 1 inserted into the blood vessel 46 and inflated to expand the inside diameter 54 (ID) of the blood vessel 46 at the location of the lesion 50. Expanding the ID 54 of the blood vessel 46 facilitates improved blood flow through the blood vessel after the catheter 10 is removed.

The balloon 20 has a working length 60 which is defined between the balloon ends 22 and 24. The ends 22 and 24 are generally symmetrical in shape. The balloon 20 has a tapered portion 62 which extends between each end 22 and 24. The tapered portion 62 is formed integral with the working length 60, and the catheter tube 18. The tapered portion 62 and the catheter tube 18 meet to form the taper angle α.

Figure 5:
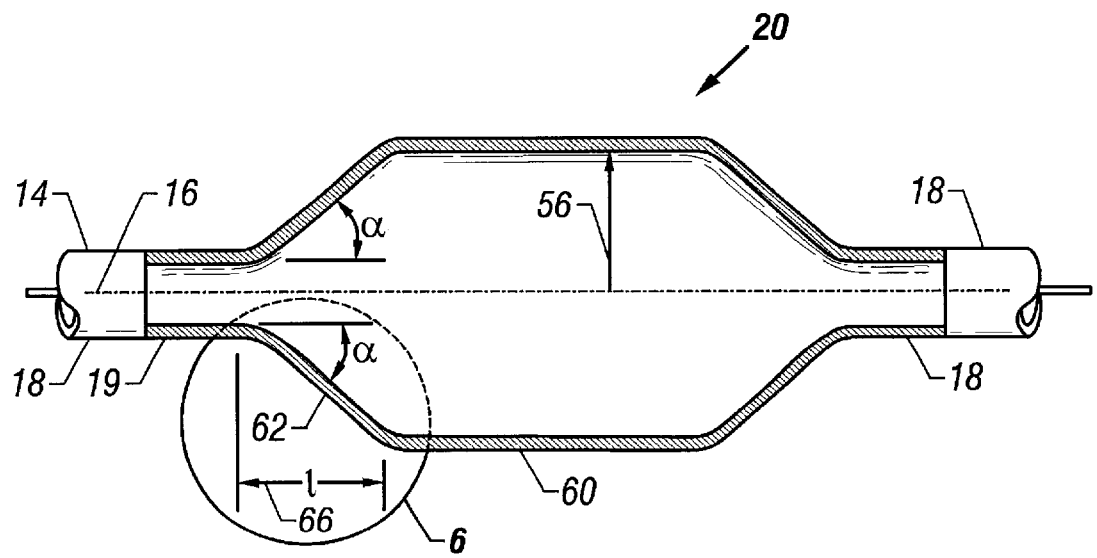
FIG. 5 is a cross-sectional view of the balloon of FIG. 3c as seen along the line 5—5 in the direction of the arrows.

With particular reference to FIG. 5, there is shown the collapsed balloon 20 of FIG. 3c in cross-section as seen facing a flat portion of the balloon 20. The distal end 14 of the catheter tube 18 abuts the balloon shaft 19. The tapered portion 62 defines a taper length 66. The taper length 66 extends a distance "I". In one embodiment, the distance "I" is within the range of 3 mm to 9 mm. In another embodiment, the distance "I" is within the range of 5 mm to 7 mm. The distance "I" is measured parallel to the catheter axis 16.

The working length 60 of the balloon 20 has a generally uniform radius 56. The radius 56 extends between the axis 16 and the working length 60. During use, the working length 60 applies radial pressure to the inside diameter of the blood vessel when the balloon 20 is in the expanded configuration. In one embodiment, the working length 60 has a generally cylindrical shape when the balloon 20 is in the expanded configuration. It can be appreciated, however, that the shape of the working length 60 can be adapted to any shape suitable for the desired purpose of the balloon 20.

The tapered portion extends from the catheter tube 18 at the taper angle α. The taper angle α is between 7° and 20°. According to one aspect of the invention, the taper angle α is between 9° and 12°. According to another aspect of the invention, the taper angle α is between 10° and 11°.

Figure 6:
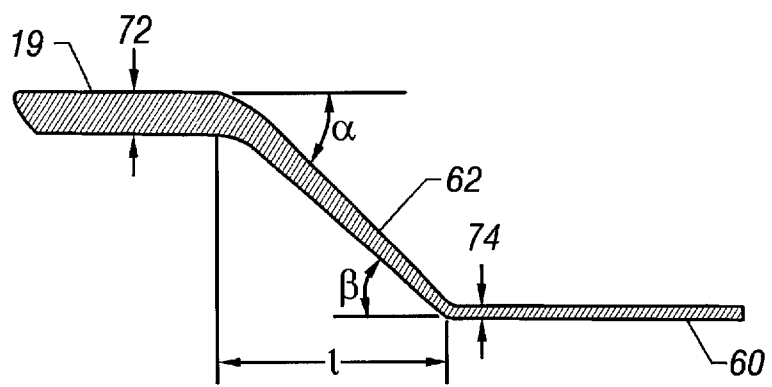
FIG. 6 is an enlarged cross-sectional view of the tapered portion of the balloon of FIG. 5 as encircled by the circle 6.

With particular reference to FIG. 6, there is shown an expanded view of the tapered portion 62 of the balloon 20 of FIG. 5. The tapered portion 62 is encircled by the circle 6 in FIG. 5. The angle α is the angle at which the tapered portion 62 extends from the balloon shaft 19. The angle β indicates the angle at which the tapered portion 62 meets the working length 60. According to one aspect of the invention, the angles α and β are equivalent angles and the working length 60 parallels the catheter tube 18.

The balloon shaft 19 has a thickness 72. The working length 66 has a thickness 74. The thickness 72 of the catheter tube 18 is greater than the thickness 74 of the working length 60. The tapered portion 62 tapers from the balloon shaft 19 to the working length 60.

Figure 7:
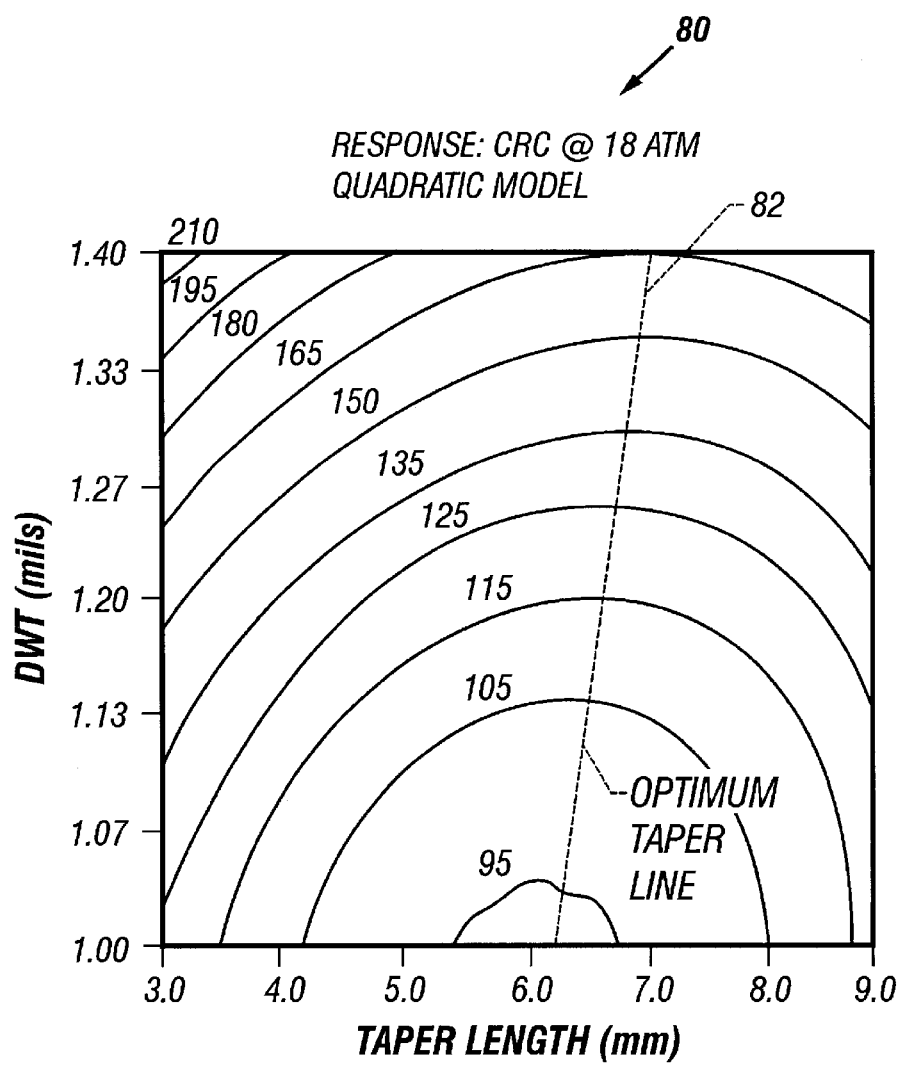
FIG. 7 is a graphic representation of the relationship of double wall thickness and optimum taper length.

When the balloon 20 is in the collapsed configuration the balloon 20 double wall thickness (DWT) may be measured. The DWT of the balloon is defined and calculated to be average double the thickness 72 of the working length. Preferably, the DWT is within the range of 1.0 mils to 1.4 mils as shown in FIG. 7 and depends on the material which the balloon 20 is made from. The DWT is generally measured by a snap gauge applied across the flat portion of a collapsed balloon.

With particular reference to FIG. 7, there is shown a diagram of a quadratic model for cross-recross forces generally designated with the reference numeral 80. It is known that the double wall thickness is a factor in determining optimal taper length. An example of an optimum taper angle line quadratic model for cross-recross forces at 18 atm balloon inflation pressure. Taper length and double wall thickness are related to the CRC forces. Accordingly, the optimum taper length is directly related to the balloon DWT. The optimum taper length is shown with reference numeral 82

Figure 8:
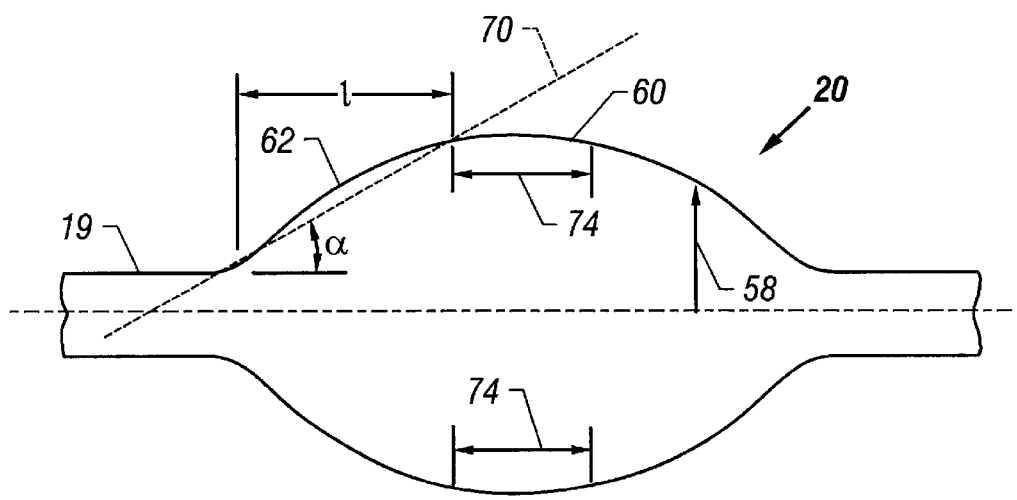
FIG. 8 is an enlarged cross-sectional view of a variation of balloon of FIG. 4.

With particular reference to FIG. 8, there is shown a variation of the balloon 20 of FIG. 1. The balloon 20 has a rounded cross-section with a varied radius 58. The tapered portion 62 defines an arc between the balloon shaft 19 and the working length 60. The tapered portion 62 has an average slope. The taper angle α equals the average slope of the tapered portion 62. The average slope is depicted by the dotted line 70. The working length 60 extends between the arrows 74.

While the foregoing detailed description has described several embodiments of the balloon 20 in accordance with this invention, it is to be understood that the above description is illustrative only and not limiting of the disclosed invention. The balloon 20 may be used in any number of devices.

The working length may connect with the catheter tube in a number of ways which are included within the scope of the claims. On way includes using an intermediary member such as a balloon shaft attached to at least one end of the balloon and which connects to the catheter tube. In this variation, the balloon shaft functions as an intermediary to connect the tapered portion with the catheter tube.

It will be appreciated that the embodiments discussed above and the virtually infinite embodiments that are not mentioned could easily be within the scope and spirit of this invention. Thus, the invention is to be limited only by the claims as set forth below.

What is claimed is:

1. A balloon dilation catheter for use in a blood vessel having a lesion, comprising:

a catheter tube having an axis;

a balloon disposed about a portion of the catheter tube, the balloon having two ends and a working length therebetween, each end including a tapered portion, each tapered portion being attached to the catheter tube, the balloon being inflatable from a collapsed conformation, wherein the working length and at least a portion of each tapered portion are substantially flattened, to an inflated conformation;

a tapered portion of the balloon in the collapsed conformation defining an edge, the edge defining an acute angle relative to the axis of the catheter tube;

the same tapered portion of the balloon in the inflated conformation defining an acute angle relative to the axis of the catheter tube, the angle being of substantially the same measure as that defined by the edge when the balloon is in the collapsed conformation.

2. A balloon dilation catheter as set forth in claim 1, wherein a portion of the working length and a portion of each taper of the balloon in the collapsed conformation are curled and the curled portions become uncurled when the balloon is in the inflated conformation, whereby the taper angles are maintained at constant measure during inflation and deflation of the balloon.

3. A balloon dilation catheter as set forth in claim 1, wherein the edge defines an angle measuring between 7° and 20° relative to the axis of the catheter tube.

4. A balloon dilation catheter as set forth in claim 1, wherein the edge defines an angle measuring between 9° and 12° relative to the axis of the catheter tube.

5. A balloon dilation catheter as set forth in claim 1, wherein the edge defines an angle measuring between 10° and 11° relative to the axis of the catheter tube.

* * * * *

UNITED STATES PATENT AND TRADEMARK OFFICE
CERTIFICATE OF CORRECTION

PATENT NO. : 6,251,094 B1
DATED : June 26, 2001
INVENTOR(S) : Bleam

It is certified that error appears in the above-identified patent and that said Letters Patent is hereby corrected as shown below:

Column 2,
Line 2, delete "200" and replace with --20°--.

Column 6,
Line 10, delete "ca" and insert -- $\alpha$ --.

Signed and Sealed this

Twenty-sixth Day of March, 2002

Attest:

*Attesting Officer*

JAMES E. ROGAN
*Director of the United States Patent and Trademark Office*